United States Patent [19]

Swanson

[11] 4,211,106
[45] Jul. 8, 1980

[54] ESTIMATES OF PERMEABILITY FROM CAPILLARY PRESSURE MEASUREMENTS

[75] Inventor: Benjamin F. Swanson, Houston, Tex.
[73] Assignee: Shell Oil Company, Houston, Tex.
[21] Appl. No.: 944,046
[22] Filed: Sep. 20, 1978
[51] Int. Cl.² ............................................. G01M 3/00
[52] U.S. Cl. ...................................................... 73/38
[58] Field of Search ........................................... 73/38

[56] References Cited

U.S. PATENT DOCUMENTS

| | | | |
|---|---|---|---|
| 2,604,779 | 7/1952 | Purcell | 73/38 |
| 2,641,924 | 6/1953 | Reichertz | 73/38 |
| 2,829,515 | 4/1958 | Johnson | 73/38 |
| 3,199,341 | 8/1965 | Heuer, Jr. et al. | 73/38 X |
| 3,859,843 | 1/1975 | Lowell | 73/38 |
| 3,882,714 | 5/1975 | Libal et al. | 73/38 |

Primary Examiner—Donald Watkins
Assistant Examiner—Joseph W. Roskos

[57] ABSTRACT

A method and apparatus for determining the permeability of small rock samples by mercury capillary pressure measurements. The apparatus comprises a measuring cell having a very small volume and means for measuring the displacement of mercury in a sample placed in the cell to at least one ten thousandth of the cell volume. The method comprises plotting the capillary pressure versus saturation as a percentage of bulk volume and using a nomogram to determine permeability of the sample.

10 Claims, 7 Drawing Figures

ESTIMATES OF PERMEABILITY FROM CAPILLARY PRESSURE MEASUREMENTS

BACKGROUND OF THE INVENTION

The present invention pertains to a method and an apparatus for improved estimates of permeability of rock samples from capillary pressure measurements. In particular, the present invention provides an improved method for estimating the permeability of formations penetrated by borehole utilizing drill bit cuttings or sidewall core samples. In an evaluation of a formation penetrated by a borehole to determine whether it is capable of commercial production, two measurements are of importance; the formation porosity and formation permeability. The porosity of the formation is related to the amount of gas or oil contained in a formation while the measurement of permeability is an indication of the producibility of the trapped gas or oil. In particular, permeability of a reservoir of rock may be defined as the fluid conductivity or the ability of fluid to flow within its interconnected pore network. If there is no innerconnection between the pores, obviously the formation has zero permeability even though the formation porosity is high. Thus, there is no natural relationship between the permeability and the porosity of a formation.

U.S. Pat. No. 2,604,779 describes an apparatus and method for measuring the capillary pressure versus saturation of rock samples. In particular, the patent describes a system using a non-wetting liquid such as mercury for determining the capillary pressure versus saturation of the rock sample. The use of a nonwetting liquid provides a means for rapidly determining sufficient points along the saturation versus pressure curve to accurately define the curve. The inventor, W. R. Purcell, described in a paper in AIME Technical Publication No. 2544 of 1949 how measurements using mercury capillary pressures could be used to calculate the permeability of rock samples. In particular, the approach is to integrate the curve of mercury saturation versus the reciprocal of the capillary pressure squared. Obviously this approach involved detailed calculations and Purcell's approach was improved upon by various workers. One of the improvements was the observation that a log-log plot of capillary pressure versus saturation approximated a hyperbola and a mathematical expression for the capillary saturation data could be developed. Further, the hyperbolic functions could be related directly to permeability. While this was an improvement, it still required considerable calculations.

Also, the use of hyperbolic functions does not correlate with capillary pressure measurements made on small rock samples such as drill bit cuttings. The plateau of the curve in the low mercury saturation region is poorly defined and does not correlate with a hyperbola. Thus permeability estimates based on hyperbolic functions using data obtained from small rock samples results in overly optimistic estimates of the permeability. As a result, the formations which at one time appeared to be commercial are, in fact, not commercial formations.

BRIEF DESCRIPTION OF THE PRESENT INVENTION

The present invention solves the above problems by providing an apparatus that is capable of more accurate measurements of capillary pressure versus mercury saturation of small rock samples. In particular, the apparatus can utilize the small chips such as drill bit cuttings that return to the surface in the mud stream. The invention also provides a method for utilizing the more accurate measurement to rapidly predict the effective permeability of the formations. The method utilizes a nomogram which may be placed directly over a log-log plot of the saturation versus capillary pressure curve to read directly the effective permeability of the formation.

The nomogram was derived from a consideration of a large number of rock samples, in particular, the saturation versus capillary pressure curves of the rock samples in correlation with their initial nonwetting phase saturation versus residual nonwetting phase saturation for a two-phase relationship. From these considerations it is easily established that the use of the nomogram provides more accurate results than the former methods which relied upon detailed mathematical calculations.

BRIEF DESCRIPTION OF THE DRAWINGS

The present invention will be more easily understood by those skilled in the art from the following detailed description of a preferred embodiment when taken in conjunction with the attached drawings in which.

PREFERRED EMBODIMENT

Figure 1:
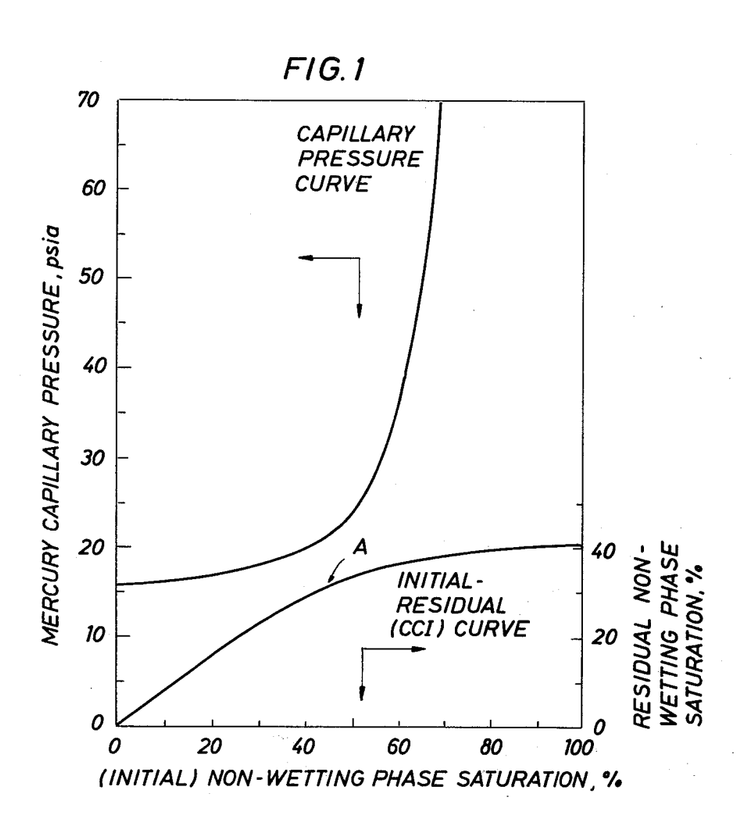
FIG. 1 is a plot of the saturation versus capillary pressure correlated with the initial nonwetting phase saturation versus residual phase saturation of a theoretical rock sample.

Referring now to FIG. 1, there is shown at the bottom a plot of the initial nonwetting phase saturation versus the residual nonwetting phase saturation for a two-phase relationship. In particular, the curve illustrates the relationship between initial and residual saturations when a nonwetting liquid such as mercury is used to saturate an evacuated rock sample or core. Above the initial-residual phase saturation curve is shown a plot of the capillary pressure versus saturation for the same sample. From an inspection of the initial-residual saturation curve it is observed to be linear to approximately the Point A corresponding to an initial saturation of approximately 42%. From this point on, the curve tends to flatten out and thus increase in the percentage saturation results in very little increase in the residual nonwetting saturation. Thus, Point A corresponds closely to the effective or useful permeability of the rock sample. At this point all of the pore spaces controlling the bulk flow through the rock will be filled and only the fine structured trapping or intrusion of the nonwetting phase in the corners of the pores is still available. Also, as observed in the capillary pressure-saturation curve, lower bulk saturations corresponding to lower mercury saturation are not representative of pore sizes which control the bulk flow through the rock. Capillary pressure corresponding to the effective permeability is that pressure which corresponds to the saturation where the pore size is effectively innerconnected and the major pore system is filled. At this point the capillary pressure corresponds to the permeability that effectively dominates a fluid flow through the sample. Again, this point corresponds to approximately Point A on the initial versus residual saturation curve or approximately 20 psia mercury capillary pressure.

From the above, it is seen that a saturation to about 42% applies to the effective pore space contributing to the fluid flow which corresponds to a capillary pressure of 20 psi. This capillary pressure is required to effectively connect all the pore space which will contribute to the dominate fluid flow through the sample. Since previous workers have established that empirical relationships can be found between parameters of this general type and permeability, a formula can be developed for predicting effective permeability of the sample. In particular, the reciprocal of the capillary pressure is proportioned to the pore size which connects the effective pore space and the product of bulk saturation and the reciprocal of the capillary pressure can be related to permeability. While this is possible, it would result in a detailed mathematical approach to the problem and have all of the difficulties of the prior art methods.

Figure 2:
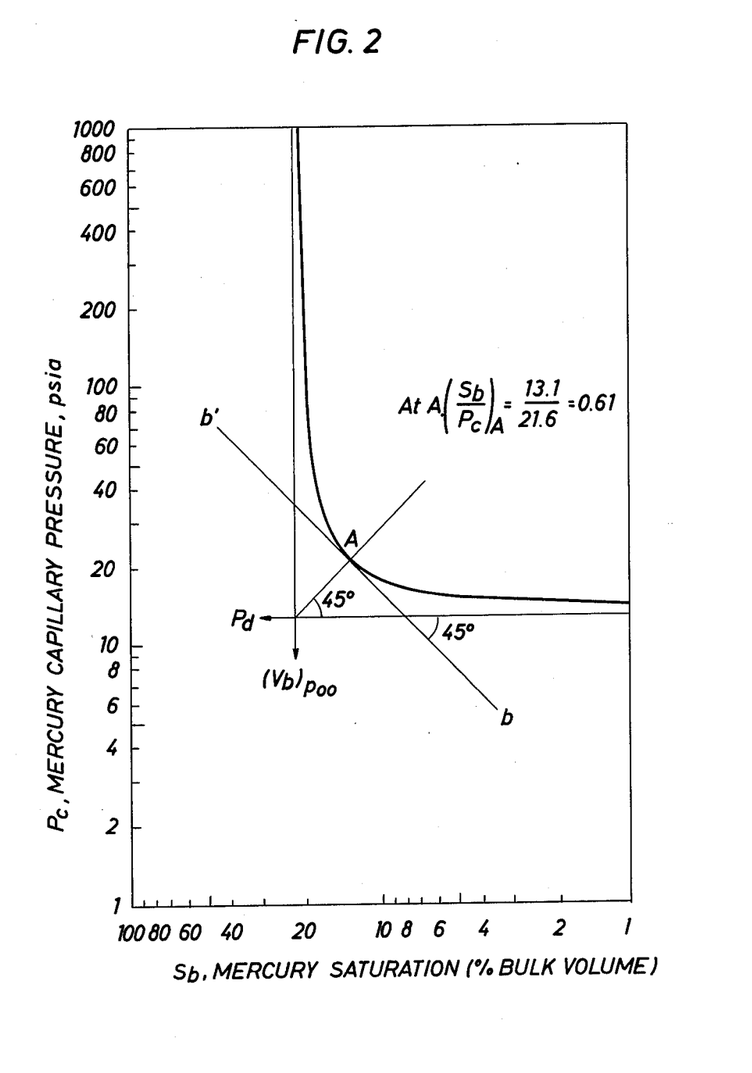
FIG. 2 is a log-log plot of the saturation versus capillary pressure curve shown in FIG. 1.

Referring now to FIG. 2, there is shown a log-log plot of the saturation versus capillary pressure shown in FIG. 1. Point A in this curve approximately corresponds to the maximum curvature of the hyperbolic equivalent of the capillary pressure versus saturation and is found at the intersection at the hyperbola and a 45-degree line passing through the origin of the hyperbolic axes. The ratio of coordinates of this point which is a function of the effective pore space times the effective pore size has a maximum value.

From an inspection of the Point A shown in FIG. 2 with Point A shown in FIG. 1, it is seen that they correspond closely since the Point A of FIG. 1 corresponds to approximately 20 psi capillary pressure while the Point A of FIG. 2 corresponds to the capillary pressure of 21.6. This relationship between the point of maximum curvature of the hyperbolic equivalent of the capillary pressure curve and the point of effective permeability was confirmed by an examination of a large number of rock samples. It is easier to choose the Point A corresponding to the maximum product of percent bulk saturation times the reciprocal capillary pressure as the parameter to be correlated with permeability rather than using the detailed mathematic approaches suggested by prior workers.

Figure 3:
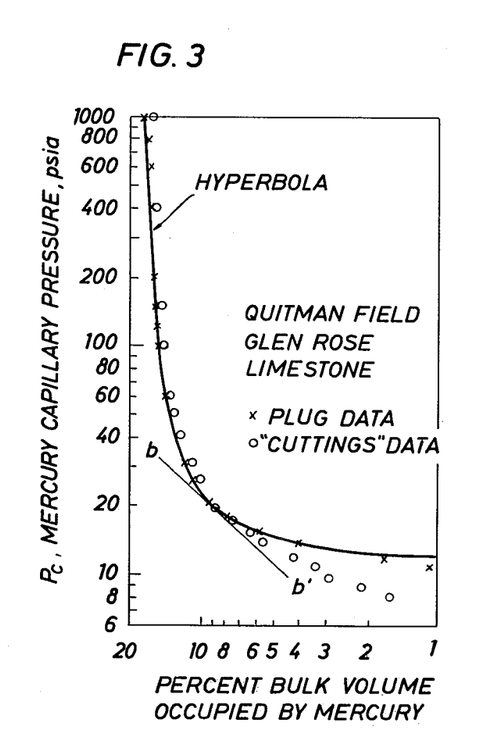
FIG. 3 is a plot of the saturation versus capillary pressure of an actual rock sample showing the deviation of the data from drill bit cuttings in low saturation regions.

Referring now to FIG. 3 there is shown a log-log plot of the bulk saturation versus capillary pressure for a particular limestone sample. In particular, there is on the plot, data for plug or cores and data from rock chips similar to drill bit cuttings. As is easily seen, the data corresponds closely in the regions of high bulk saturation and high capillary pressures but deviates considerably in the low capillary pressure and low saturation region. Also shown is a solid line representing a hyperbola calculated from the core data. From this representation it is seen that the tangent point of the 45-degree line is the same for both curves. Thus utilizing the method of the present invention it is possible to accurately determine the effective permeability using extremely small rock samples such as drill bit cuttings.

Figure 4:
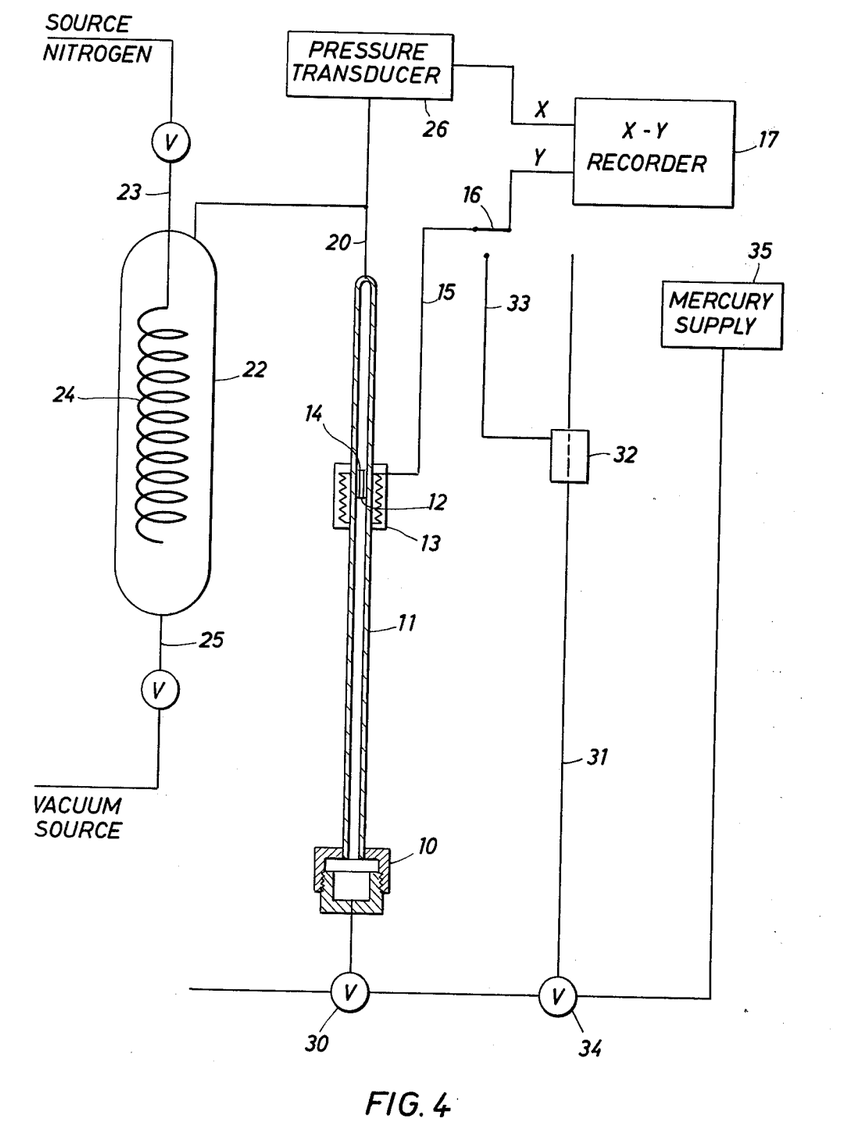
FIG. 4 shows the detailed construction of the apparatus.

Referring now to FIG. 4, there is shown the detailed construction of an apparatus suitable for obtaining accurate measurements of the saturation versus capillary pressure using extremely small samples. The sample chamber 10 may be comprised of two cup members having mating male and female threads to provide an easy means for opening the same chamber to insert the rock chips.

The sample chamber 10 is connected to a manometer tube 11 having a linear displacement transformer 13 for measuring the mercury level in the manometer. The manometer tube is preferably of small diameter so that small displacements may be accurately measured. A tube having a volume of 0.015 cubic centimeters per centimeter of length will give good results when the gross volume of the sample is 0.05 to 0.10 cubic centimeters. In particular, a soft iron slug 12 floats on the top of the mercury 12 and produces a signal in the linear displacement transformer 12. The transformer signal is supplied by lead 15 to one position of a two position switch 16 whose movable member is coupled to a Y input of the XY recorder 17. The top of the manometer tube is coupled by a tube 20 to a pressure transducer 26 and to a source of pressurized gas contained in a vessel 22. The vessel 22 is supplied with pressurized gas from a nitrogen source through a line 23 and an evaporation coil 24 is provided for vaporizing the nitrogen in order to gradually increase the pressure in vessel 22. The vessel 22 is also coupled to a vacuum source by means of a line 25 so that the test may be initiated with vessel 22, chamber 10 and tube 11 at zero absolute pressure. The vaccum or pressure in the manometer column is measured by a pressure transducer 26 whose output signal is applied to the X axis of the recorder. Thus the recorder will provide a plot of the displacement of the mercury corresponding to the percent saturation of the sample along the Y axis and the corresponding pressure along the X axis. The system is supplied with mercury from a source 35 through suitable control valves 34 and 30. The control valve 34 is also coupled to a vertical manometer tube 31 having a linear displacement transformer 32 mounted thereon. The signal from the linear displacement transformer 32 is coupled by a lead 33 to the other contact to the twopositioned switch.

In operation cell 10 is drained of mercury through valve 30 while the manometer column 31 is filled of mercury from the supply 35. After the system is drained, the valve 30 is closed and vacuum is applied through line 25. Valves 30 and 34 are positioned to fill the chamber 10 and column 11 with mercury from the column 31. The quantity of mercury used is measured by the linear displacement transformer 32. The pressure on the column 11 is increased gradually by bleeding nitrogen into vessel 22 and a recording of mercury displaced versus pressure obtained. This recording is referred to as the cell blank and provides a measurement of the amount of mercury displacement due to stretch of the materials used in making the cell. The cell and column are drained again. The rock samples are then placed in the sample chamber 10, the chamber connected to the manometer column 11 and a vacuum drawn on chamber 10. Valves 30 and 34 are then positioned so that mercury from the manometer column 31 may be used to fill the sample chamber and the manometer column 11 to a predetermined level. From previous measurements of the volume of mercury required to fill the system and the volume required to fill the system with the samples in the sample chamber 10, one can determine the gross volume of the sample chips. This of course, is recorded on the XY recorder to provide a basis for determining the percent of mercury saturation of the samples. Valves 30 and 34 are then closed and pressure applied to the top of the manometer column 11 to force the mercury into the sample. The displacement of the mercury into the sample is measured by the linear displacement transformer 13 which is recorded in correlation with the pressure. These measurements thus provide an accurate measurement of the mercury saturation as a percentage of the volume of the samples in relation to the pressure applied.

Figure 5:
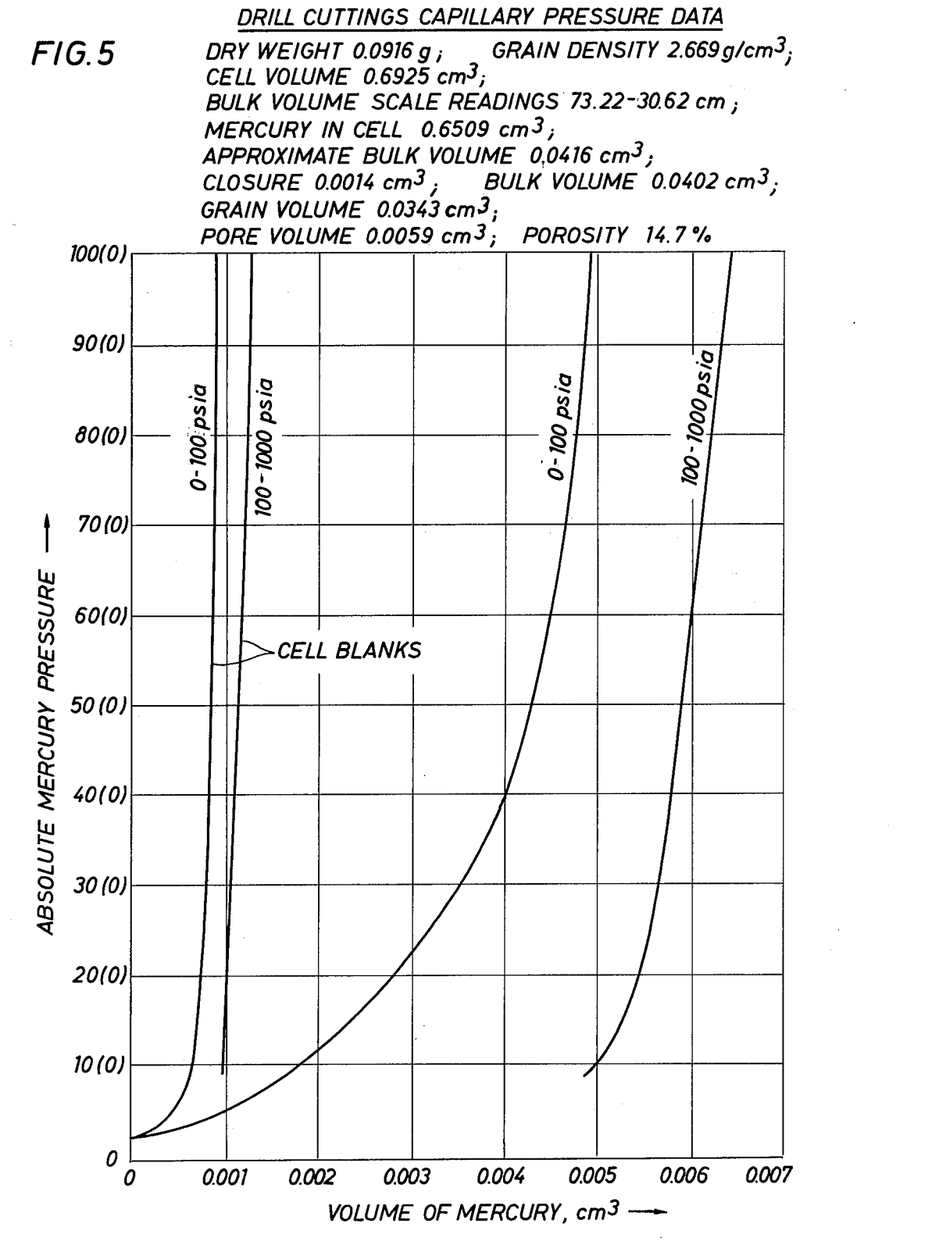
FIG. 5 is a set of recordings obtained with the apparatus of FIG. 4.
Figure 6:
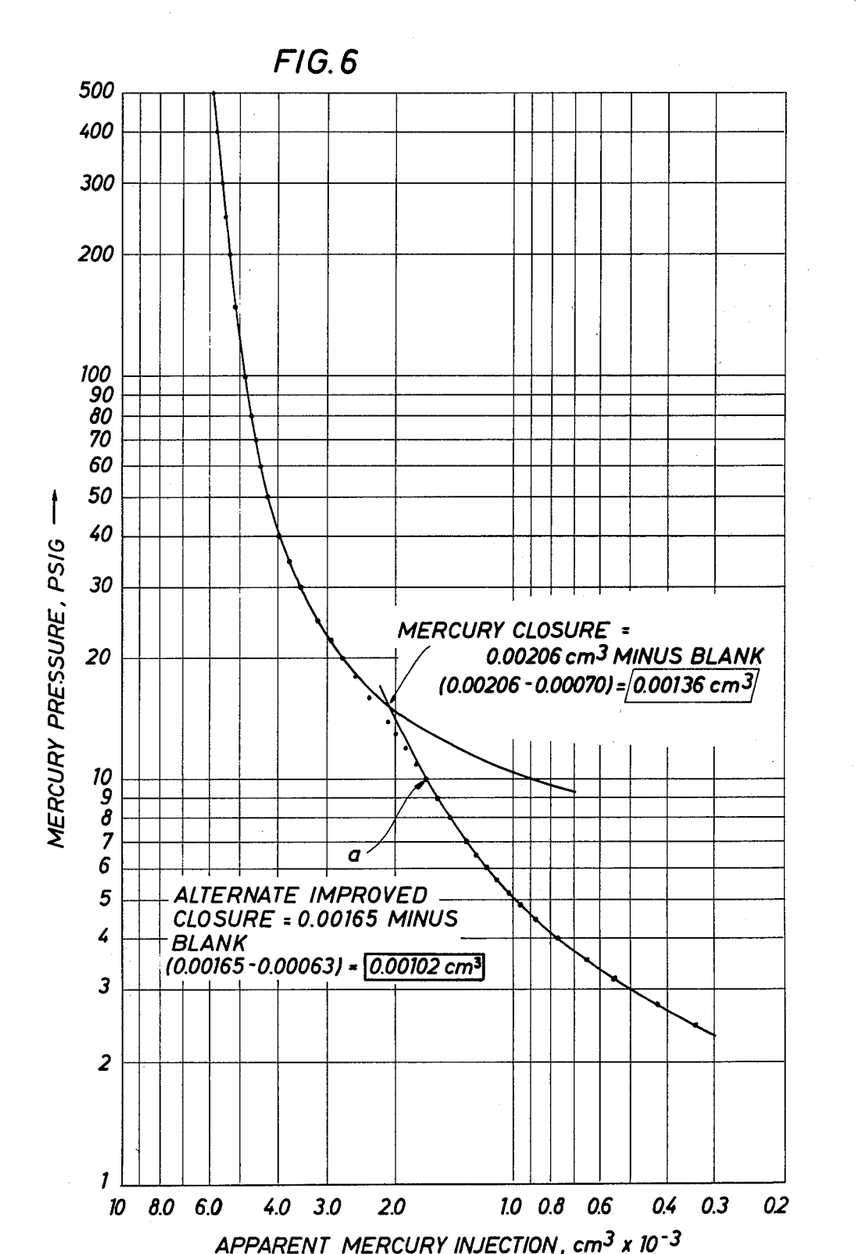
FIG. 6 is a log-log plot of the data of FIG. 5.
Figure 7:
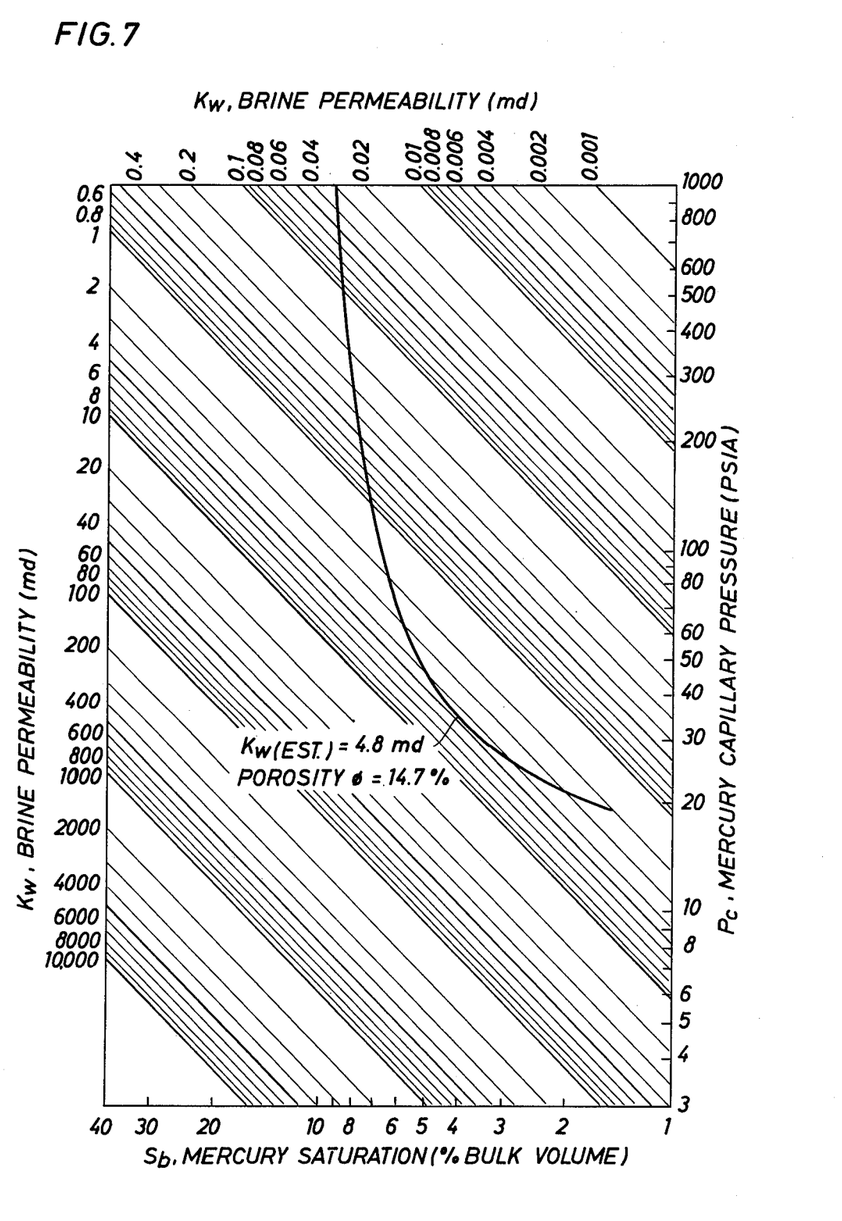
FIG. 7 shows a saturation versus capillary curve overlaid with a nomogram of the present invention for the data of FIG. 5.

Referring now to FIGS. 5, 6 and 7 there is shown the recorded data in FIG. 5 and plots of the data in 6 and 7 that are used to determine the brine permeability of the sample. In FIG. 5 there is shown the data relating to the drill cuttings used to obtain the data shown in FIG. 5. In particular, the weight of the drill cuttings and the cell volume are shown together with the porosity of the sample. The chip volume is determined by taking the difference between the readings in the height of the column 31 when the cell and column 11 are filled with mercury to the same levels with the chips in the cell and without the chips. From these measurements one can determine the bulk volume of the chips. The data shown in FIG. 5 includes both the cell blank data at the left and the actual data to the right which is obtained when the drill cuttings are in the cell. The drill cuttings measurements minus the cell blank measurements from FIG. 5 plotted on a log-log plot in FIG. 6 to produce two separate curves which closely approximate hyperbolas. Where the two curves of FIG. 6 cross is called the closure point and assumed to be the point at which the mercury has completely closed around the individual chip samples. Only the data from this point on is used to determine the brine permeability. An improved method of defining the closure point is to select the inflection point in the mercury injection curve. The inflection point is noted at Point A in FIG. 6 and can be obtained from the derivative of the curve. While the improved method for determining the closure point provides greater accuracy, acceptable results are obtained using the crossing point. The data from FIG. 6 is plotted on a preprinted nomogram in FIG. 7. As easily seen from this plot, the brine permeability is approximately 4.8 millidarcies.

The above procedure can be performed using extremely small drill cuttings as samples. Also the method can be used with larger samples by crushing the sample to obtain small pieces.

I claim as my invention:

1. A method for determining the permeability of a small rock sample comprising:
   obtaining a series of measurements of mercury saturation as a percentage of the bulk volume of the sample versus the mercury capillary pressure applied to the same;
   plotting said series of measurements on a log-log scale chart;
   determining the brine permeability of the sample using a nomograph formed by obtaining a large number of log-log plots of mercury capillary pressure versus mercury saturation for various types of rock samples;
   plotting the tangent point of a 45-degree line on each plot;
   using the coordinates of the tangent point to determine the brine permeability from the emperical formula $$K_w = 355 \frac{(S_b)}{P_c A} 2.005$$

where $K_w$ is the brine permeability and $S_b$ and $P_c$ are the saturation and capillary pressure at the tangent point; and,
   plotting said 45-degree tangent lines on a nomograph having coordinates of capillary pressure versus saturation on two sides and brine permeability on the two opposite coordinates.

2. The method of claim 1 wherein said mercury saturation versus capillary pressure measurements are made using a total sample volume including both the rock samples and mercury of less than one cubic centimeter.

3. The method of claim 2 wherein said mercury saturation measurements are made by measuring the flow of mercury into the total sample volume with a precision of at least $5 \times 10^{-6}$ cubic centimeters.

4. An apparatus for making mercury capillary pressure versus mercury saturation measurements on very small rock samples, said apparatus comprising:
   a sample cell, said cell having a volume of less than one cubic centimeter;
   a manometer column coupled to said cell;
   valve means disposed to couple said sample cell to a vacuum source or fill said monometer and sample cell with mercury;
   a source of pressurized fluid, means for selectively coupling said source to said manometer to displace mercury from said manometer into said cell; and,
   measuring means comprising a linear displacement transformer whose output voltage varies linearly with the displacement of its movable core, said transformer being disposed to surround the mercury column in said manometer and said movable core being disposed to float on the top of the mercury column.

5. The apparatus of claim 4 wherein said linear transformer is disposed to be moved along the outer surface of said manometer.

6. The apparatus of claim 4 wherein said manometer tube comprises a calibrated tube having an approximate volume of 0.015 cubic centimeters per centimeter of length.

7. The apparatus of claim 4 wherein said pressurized gas is nitrogen.

8. The apparatus of claim 4 and in addition a second manometer coupled to said sample cell and disposed to measure the volume of mercury displaced from said sample cell by said rock samples.

9. An apparatus for making mercury capillary pressure versus mercury saturation measurements on very small rock samples, said apparatus comprising:
   a sample cell, said sample cell having a volume of less than one cubic centimeter;
   a manometer column coupled to said sample cell and disposed above said cell;
   a closed chamber, said closed chamber being coupled to the top of said manometer column;
   a source of pressurized gas, said source of pressurized gas being coupled to said closed chamber;
   a source of vacuum, said source of vacuum being coupled to said closed chamber;

valve means, said valve means being disposed to control the coupling of said source of pressurized gas and said source of vacuum to said closed chamber;

a pressure control means, said pressure control means being disposed to control the pressure in the coupling between said closed chamber and said manometer;

means coupled to the bottom of said sample cell for selectively filling said sample cell and manometer with mercury;

a second manometer, said second manometer being coupled to the bottom of said sample cell to measure the volume of mercury displaced by a sample placed in said sample cell; and, means for recording the pressure with mercury displaced when said rock samples are saturated with mercury at various pressures.

10. The apparatus of claim 9 wherein a linear displacement transformer is disposed on the outer surface of each manometer and a soft iron core is disposed inside of each manometer to measure the displacement of mercury from said manometers.

* * * * *